United States Patent
Cooper et al.

(10) Patent No.: US 6,626,908 B2
(45) Date of Patent: Sep. 30, 2003

(54) PEDICLE ATTACHMENT ASSEMBLY

(75) Inventors: Derek Redvers Cooper, Berkshire (GB); Simon Nicholas Collins, Gloucestershire (GB); Ian James Emslie, Gloucestershire (GB); David Mark Fletcher, Gloucestershire (GB)

(73) Assignee: Corin Spinal Systems Limited, Cirencester (GB)

( * ) Notice: Subject to any disclaimer, the term of this patent is extended or adjusted under 35 U.S.C. 154(b) by 33 days.

(21) Appl. No.: 09/893,704

(22) Filed: Jun. 29, 2001

(65) Prior Publication Data

US 2002/0010467 A1 Jan. 24, 2002

(30) Foreign Application Priority Data

Jul. 22, 2000 (GB) .............................. 0017924
Apr. 18, 2001 (GB) .............................. 0109464
Apr. 3, 2001 (GB) .............................. 0108270

(51) Int. Cl.$^7$ .................... A61B 17/56; A61B 17/58; A61F 2/30
(52) U.S. Cl. ...................................................... 606/61
(58) Field of Search ................ 606/60, 61, 72

(56) References Cited

U.S. PATENT DOCUMENTS 5,681,319 A 10/1997 Biedermann et al.
5,797,911 A 8/1998 Sherman et al.
5,817,094 A 10/1998 Errico et al.
5,882,350 A * 3/1999 Ralph et al. .................. 606/61
6,440,137 B1 * 8/2002 Horvath et al. ............... 606/73

FOREIGN PATENT DOCUMENTS

| EP | 0 947 174 | 10/1999 |
| WO | 98/27884 | 7/1998 |
| WO | WO 98/27884 | 7/1998 |
| WO | 01/22893 A1 | 5/2001 |

* cited by examiner

Primary Examiner—Tuan N. Nguyen
(74) Attorney, Agent, or Firm—Young & Thompson

(57) ABSTRACT

A pedicle attachment assembly includes a pedicle attachment device having a head. A polyaxial housing has a through bore comprising a base portion and two posts upstanding from the base portion, the posts defining therebetween a slot for receiving a rod. A saddle-shaped element is disposable in the slot and has a part cylindrical recess in an upper surface for engagement in use with the rod. The saddle-shaped element has a convex lower portion for engagement in a complimentary concave recess in an upper surface of the head of the attachment device. The lower surface of the head of the attachment device and the lower end of the through bore in the housing have complementary part spherical surfaces for engagement with one another. A cap assembly is provided for clamping the rod in the housing.

8 Claims, 2 Drawing Sheets

PEDICLE ATTACHMENT ASSEMBLY

INTRODUCTION

This invention relates to a pedicle attachment assembly for use in conjunction with a rod for immobilising bone segments, particularly in the spine, so as to allow the segments to fuse together.

To achieve bone fusion or arthrodesis a stable environment has to be created. The pedicle attachment and rod assembly immobilises the bony junction so that bone graft of bone substitute material which is placed across the junction can consolidate. This consolidation process takes place during the healing process and creates a bony bridge or solid fusion mass across and between the bony junction. The process of arthrodesis has been well documented in the field of batch mechanics and traumatology.

SUMMARY OF THE INVENTION

According to a first aspect of the present invention there is provided a pedicle attachment assembly comprising a pedicle attachment device having a head, a polyaxial housing having a through bore and comprising a base portion and two posts upstanding from the base portion, the posts defining therebetween a slot for receiving a rod, a saddle-shaped element disposed or disposable in the slot and having a part cylindrical recess in an upper surface for engagement in use with the rod, the head of the attachment device and the lower end of the through bore having interengageable first portions and the head of the attachment device and the saddle-shaped element have interengageable second portions, the first portions and the second portions being shaped to allow the attachment device to pivot relative to the housing and the saddle-shaped element, and a cap assembly for use in clamping the rod in the housing.

According to a second aspect of the invention there is provided a pedicle screw assembly comprising a pedicle screw having a threaded stem and a head of larger diameter than the stem, a polyaxial housing having a through bore and comprising a base portion and two posts upstanding from the base portion, the posts defining therebetween a slot for receiving a rod, a saddle-shaped element disposed or disposable in the slot and having a part cylindrical recess in an upper surface for engagement in use with the rod, the lower surface of the head of the screw and the lower end of the through bore in the housing having complementary part spherical or substantially part spherical surfaces for engagement with one another, and a cap assembly for in use clamping the rod in the housing, the cap assembly comprising a cap having an internally threaded skirt portion for threadably engaging external threads provided on the two posts and a top portion having an internally threaded aperture, and a set screw engageable in the internally threaded aperture so that diametrically opposed regions of the lower edge of the cap and the set screw in use provide three point clamping between the rod and the cap assembly.

The invention will now be more particularly described, by way of example, with reference to the accompanying drawings.

DESCRIPTION OF THE PREFERRED EMBODIMENTS

Figure 1:
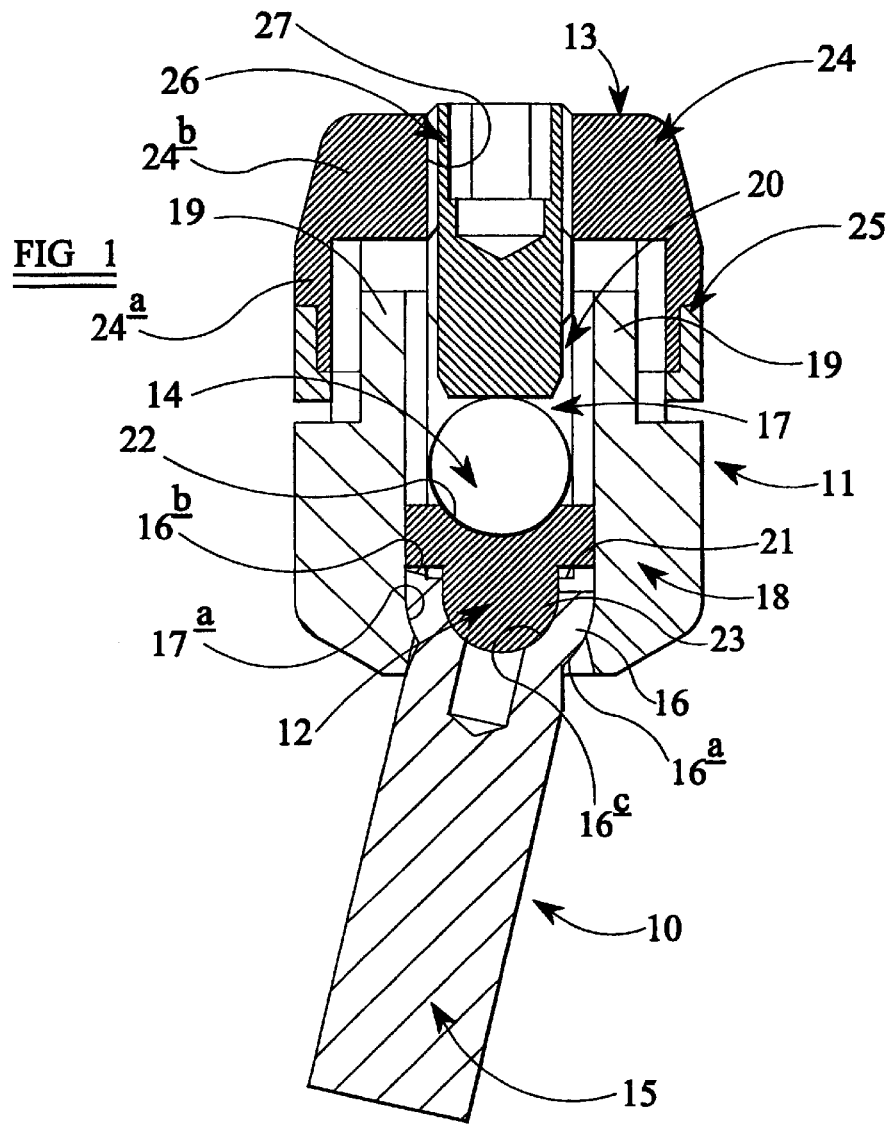
FIG. 1 is a sectional view through one embodiment of a pedicle attachment assembly according to the present invention.
Figure 2:
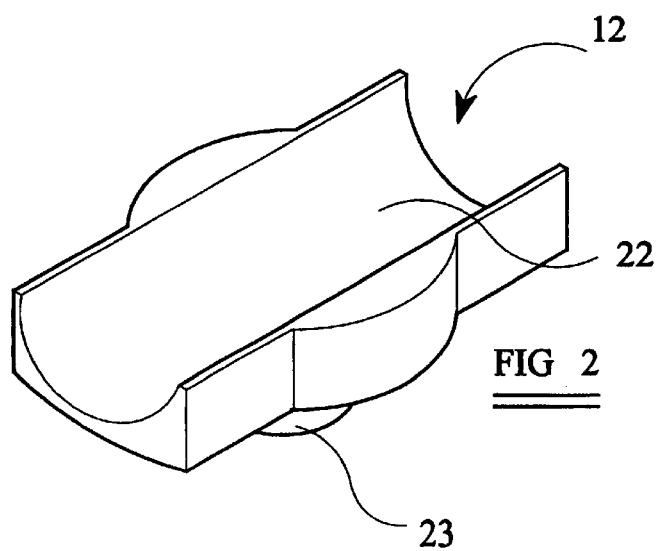
FIG. 2 is a perspective view of the saddle-shaped element of the pedicle attachment assembly shown in FIG. 1.

Referring to FIGS. 1 and 2 of the drawings, the pedicle attachment assembly shown therein is intended to be secured to bone segments of a patient's spine and comprises a pedicle attachment device in the form of a screw 10, a polyaxial housing 11, a saddle-shaped element 12 and a cap assembly 13. FIG. 1 also shows a rod 14 which is clamped to two or more pedicle screw assemblies secured to different bone segments of the spine to immobilise the segments and allow the segments to fuse together. The assembly is typically formed of titanium.

The pedicle screw 10 comprises a threaded stem 15 and a head 16 having a diameter larger than the stem.

The polyaxial housing 11 has a through bore 17 and comprises a base portion 18 and two posts 19 upstanding from the base portion, the posts 19 defining therebetween a slot 20 for receiving the rod 14. The base of the slot 20 is indicated by the reference numeral 21.

The through bore 17 has a diameter, apart from at its lowermost end, sufficient to allow the stem 15 and head 16 of the pedicle screw 10 to pass therethrough. However, the lowermost end 17a of the through bore 17 is of part spherical shape and the diameter of the opening at the lowermost end of the through bore is sufficient to allow the stem 15 but not the head 16 of the pedicle screw to pass therethrough.

The lower surface 16a of the head 16 of the screw 10 is of part spherical shape so as to be complementary with the shape of the lowermost end 17a of the through bore. This enables the screw 10 to tilt in any direction with respect to the housing 11.

The saddle-shaped element 12 is disposed in the slot 20 of the housing and extends across the entire width of the housing 11 and into the gaps between adjacent free side edges of the posts 19. This ensures that the saddle-shaped element 12 cannot be angularly displaced relative to the housing 11.

The saddle-shaped element 12 has a part cylindrical recess 22 in its upper surface, the recess 22 extending the longitudinal extent of the element 12, for engagement with the rod 14. By virtue of the fact that the saddle-shaped element 12 cannot be angularly displaced within the housing 11, the part cylindrical recess 22 is always correctly orientated to engage with the rod 14. The saddle-shaped element 12 has a convex and preferably a part spherical lower portion 23 for engagement in a complementary concave and preferably part spherical recess 16c in the head 16 of the screw 10. This enables the screw 10 to pivot with respect to the housing 11 and the saddle-shaped element 12 without vertical displacement of the saddle-shaped element 12 relative to the screw head 16 particularly where the lower portion 23 and recess 16c are part spherical. As an alternative to the above arrangement, the saddle-shaped element may have a concave and preferably a part spherical recess for engagement with a complementary convex and preferably part spherical portion on the head of the screw.

The posts 19 have a stepped external diameter and the smaller diameter ends are uppermost and are externally threaded.

The cap assembly 13 comprises a cap, having a main portion 24 and a collar 25, and a set screw 26. The main portion 24 of the cap comprises a skirt portion 24a and a top portion 24b. The skirt portion 24a is internally threaded for threadable engagement with the external threads on the upper parts of the posts 19. The upper portion 24b of the cap has a central internally threaded aperture 27 threadably engageable with an external thread on the set screw 26.

The collar 25 is of stepped internal diameter, the lower end being of smaller diameter than the upper end and corresponding in diameter to the internal diameter of the skirt portion of the cap. The collar is a push fit over an externally stepped lower portion of the cap and serves to provide, when in use contacting the rod 14, a stationary or substantially stationary downwardly directed clamping force onto the rod 14 as the main portion 24 of the cap assembly 13 is being tightened.

In use, the screw 10 is fitted in the housing 11 and the screw is then screwed into the bone. In order to enable this to be done, the head of the screw 10 may be provided with cross slots which are engaged by a screwdriver portion of a special tool. A sleeve on the tool engages the external thread on the posts 19 thus pulling the screwdriver portion and screw together and rigidly locking the screw 10 and housing 11 together in the same axis during implantation. Once the screwdriver has been released, the housing 11 will be left free to articulate on the screw head.

The saddle-shaped element 12 is then placed in the slot 20 between the posts 19 of the housing 11. The rod 14 is then placed in the slot 20 to come into contact with the part cylindrical recess 22 in the upper surface of the saddle-shaped element 12. The cap assembly 13 is then screwed down onto the posts 19 and finally the set screw 26 is screwed into the aperture 27. Diametrically opposed regions of the lower edge of the collar 25, together with the set screw 26, provide three point clamping between the rod 14 and the cap assembly 13.

A pedicle screw assembly as described above reduces the need for accurate contouring of the rod 14.

Figure 3:
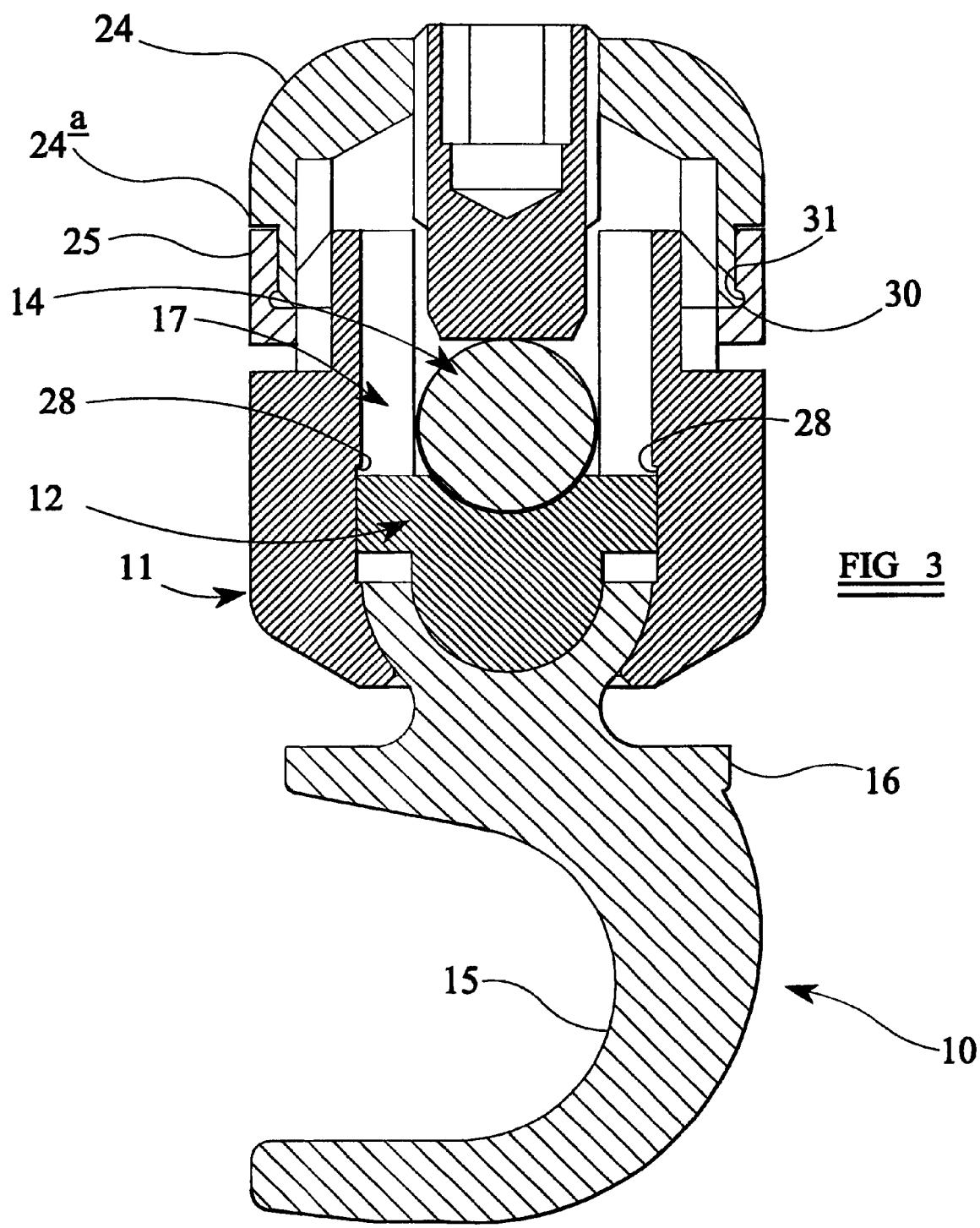
FIG. 3 is a sectional view through another embodiment of a pedicle attachment assembly according to the present invention.

Referring now to FIG. 3 of the drawings, the pedicle attachment device comprises a hook 10 comprising a hook-shaped portion 15' (instead of a threaded stem) and a head 16'. In most other respects the attachment assembly is identical to the attachment assembly of FIGS. 1 and 2. However, the saddle-shaped element 12 is held captive relative to the housing 11 by providing a slight inwards step 28 in the bore 17 above the saddle-shaped element 12. Also, the collar 25 is held captive with the main portion 24 of the cap by providing the outer surface of the skirt portion 24a of the cap with a circumferentially extending lip 30 which is received in an annular groove 31 in the inner surface of the collar 25. These two modifications could also be made to the embodiment shown in FIGS. 1 and 2 to make the saddle-shaped element of that embodiment captive relative to the housing and to make the collar captive with the main portion of the cap.

The above embodiments are given by way of example only and various modifications will be apparent to persons skilled in the art without departing from the scope of the invention as defined in the appended claims.

What we claim is:

1. A pedicle attachment assembly comprising a pedicle attachment device having a head, a polyaxial housing having a through bore and comprising a base portion and two posts upstanding from the base portion, the posts defining therebetween a slot for receiving a rod, a saddle-shaped element disposed in the slot and having a part cylindrical recess in an upper surface for engagement in use with the rod, the head of the attachment device and the lower end of the through bore having interengageable first portions and the head of the attachment device and the saddle-shaped element have interengageable second portions, the first portions and the second portions being shaped to allow the attachment device to pivot relative to the housing and the saddle-shaped element, and a cap assembly for use in clamping the rod in the housing,
wherein the cap assembly comprises a cap having an internally threaded skirt portion for threadably engaging external threads provided on the two posts and a top portion having an internally threaded aperture, and a set screw engageable in the internally threaded aperture so that diametrically opposed regions of the lower edge of the cap and the set screw in use provide three point clamping between the rod and the cap assembly.

2. The pedicle attachment assembly as claimed in claim 1, wherein the cap comprises a main portion including the top portion and an internally threaded part of the skirt portion and an internally stepped collar for fitting or fitted over the skirt portion.

3. The pedicle attachment assembly as claimed in claim 1, wherein the collar is held captive relative to the main portion of the cap.

4. A pedicle screw assembly comprising a pedicle screw having a threaded stem and a head of larger diameter than the stem, a polyaxial housing having a through bore and comprising a base portion and two posts upstanding from the base portion, the posts defining therebetween a slot for receiving a rod, a saddle-shaped element disposed or disposable in the slot and having a part cylindrical recess in an upper surface for engagement in use with the rod, the lower surface of the head of the screw and the lower end of the through bore in the housing having complementary part spherical or substantially part spherical surfaces for engagement with one another, and a cap assembly for in use clamping the rod in the housing, the cap assembly comprising a cap having an internally threaded skirt portion for threadably engaging external threads provided on the two posts and a top portion having an internally threaded aperture, and a set screw engageable in the internally threaded aperture so that diametrically opposed regions of the lower edge of the cap and the set screw in use provide three point clamping between the rod and the cap assembly.

5. The pedicle screw assembly as claimed in claim 4, wherein the cap comprises a main portion including the top portion and an internally threaded part of the skirt portion and an internally stepped collar for fitting over the skirt portion.

6. A pedicle attachment assembly comprising a pedicle attachment device having a head, a polyaxial housing having a through bore and comprising a base portion and two posts upstanding from the base portion, the posts defining therebetween a slot for receiving a rod, a saddle-shaped element disposable in the slot and having a part cylindrical recess in an upper surface for engagement in use with the rod, the head of the attachment device and the lower end of the through bore having interengageable first portions and the head of the attachment device and the saddle-shaped element have interengageable second portions, the first portions and the second portions being shaped to allow the attachment device to pivot relative to the housing and the saddle-shaped element, and a cap assembly for use in clamping the rod in the housing and comprising a cap having an internally threaded skirt portion for threadably engaging external threads provided on the two posts and a top portion having an internally threaded aperture, and a set screw engageable in the internally threaded aperture so that diametrically opposed regions of the lower edge of the cap and the set screw in use provide three point clamping between the rod and the cap assembly.

7. The pedicle attachment assembly as claimed in claim 6, wherein the cap comprises a main portion including the top portion and an internally threaded part of the skirt portion and an internally stepped collar for fitting or fitted over the skirt portion.

8. The pedicle attachment assembly as claimed in claim 6, wherein the collar is held captive relative to the main portion of the cap.

* * * * *